United States Patent [19]

Schromm et al.

[11] Patent Number: 4,647,563
[45] Date of Patent: Mar. 3, 1987

[54] HETEROCYCLIC COMPOUNDS

[75] Inventors: Kurt Schromm, Ingelheim; Anton Mentrup, Mainz-Kastel; Ernst-Otto Renth, Ingelheim; Armin Fügner, Gau-Algesheim; Ilse Streller, Dörrebach, all of Fed. Rep. of Germany

[73] Assignee: Boehringer Ingelheim KG, Ingelheim am Rhein, Fed. Rep. of Germany

[21] Appl. No.: 806,692

[22] Filed: Dec. 9, 1985

Related U.S. Application Data

[60] Division of Ser. No. 443,912, Nov. 23, 1982, Pat. No. 4,581,367, which is a division of Ser. No. 285,713, Jul. 22, 1981, Pat. No. 4,378,361, which is a continuation of Ser. No. 156,928, Jun. 6, 1980, abandoned, which is a continuation of Ser. No. 60,389, Jul. 25, 1979, abandoned.

[30] Foreign Application Priority Data

Jul. 28, 1978 [DE] Fed. Rep. of Germany ....... 2833140

[51] Int. Cl.⁴ ................. A61K 31/535; A61K 31/505; C07D 413/12
[52] U.S. Cl. .................... 514/234; 514/259; 514/351; 514/375; 514/385; 514/392; 514/394; 514/338; 514/339; 544/105; 544/285; 544/287; 546/157; 546/271; 546/276; 546/277; 546/278; 548/221; 548/260; 548/326; 548/333
[58] Field of Search ................ 544/105, 285; 548/221; 514/259, 234, 375

[56] References Cited

U.S. PATENT DOCUMENTS 3,274,194  9/1966  Hayao ................................. 544/285
3,718,648  2/1973  Beyerle et al. ...................... 544/285

Primary Examiner—Glennon H. Hollrah
Assistant Examiner—James H. Turnipseed
Attorney, Agent, or Firm—Hammond & Littell, Weissenberger & Dippert

[57] ABSTRACT

Compounds of the formula

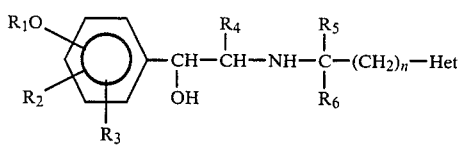

wherein
Het is

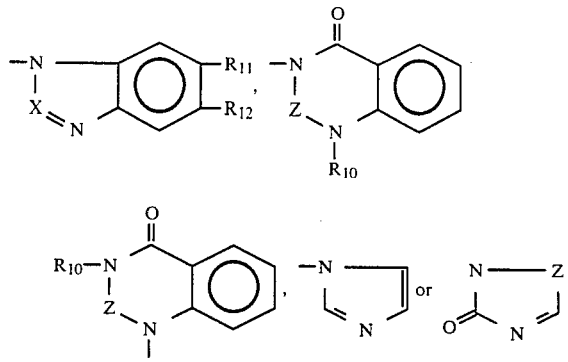

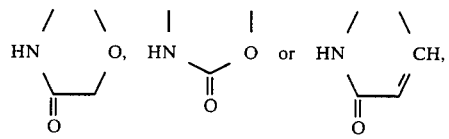

n is an integer from 1 to 4, inclusive, preferably 2 or 3,
$R_1$ is H or acyl,
$R_2$ is H, $R_1O$, $-NHSO_2R_7$, $-NHCOR_8$, $-NHCONHR_8$, $-NH-CH_2-C_6H_4-R_9$, $-CH_2OH$, $-CH_2SO_2R_7$, $-CONHR_8$, halogen or $-CN$,
$R_3$ is H, halogen, $R_7$ or $-OR_7$,
$R_2$ and $R_3$ together with each other are $$HN\diagdown O,\quad HN\diagdown O\quad\text{or}\quad HN\diagdown CH,$$
(with carbonyl linkages as shown)

$R_4$ is H, $-CH_3$ or $-C_2H_5$,
$R_5$ and $R_6$ are each H or $-CH_3$,
$R_7$ is $C_1-C_4$ alkyl,
$R_8$ is H or $C_1-C_4$ alkyl,
$R_9$ is H, $C_1-C_4$ alkyl or $C_1-C_4$ alkoxy optionally interrupted by oxygen,
$R_{10}$ and $R_{12}$ are each H, $CH_3$, Cl or $OCH_3$, or together methylenedioxy,
X is

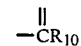

or N, and
Z is $-CH_2$ or $-CO$;

in the form of racemates, enantiomers, diastereoisomeric antipode pairs, and non-toxic, pharmacologically acceptable acid addition salts thereof. The compounds as well as the salts are useful as bronchospasmolytics, spasmolytics, muscle-relaxants, antiallergics and hypotensives.

6 Claims, No Drawings

HETEROCYCLIC COMPOUNDS

This is a division of copending application Ser. No. 443,912, filed Nov. 23, 1982, now U.S. Pat. No. 4,581,367, which in turn is a division of application Ser. No. 285,713, filed July 22, 1981, now U.S. Pat. No. 4,378,361, issued Mar. 29, 1983; which which in turn is a continuation of application Ser. No. 156,928, filed June 6, 1980, now abandoned; which in turn is a continuation of application Ser. No. 060,389, filed July 25, 1979, now abandoned.

This invention relates to novel heterocyclic compounds and salts thereof, to various methods of preparing these compounds, to pharmaceutical compositions containing them as active ingredients, and to methods of using them as broncholytics, uterus relaxants, antiallergics and hypotensives.

More particularly, the present invention relates to a novel class of heterocyclic compounds represented by the formula

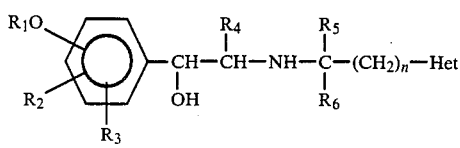

wherein Het is

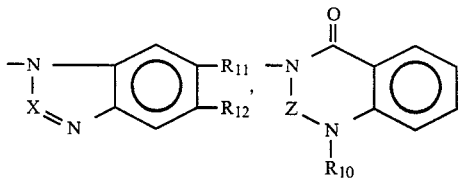

n is an integer from 1 to 4, inclusive, preferably 2 or 3, $R_1$ is H or acyl, $R_2$ is H, $R_1O$, —NHSO$_2$R$_7$, —NHCOR$_8$, —NH-CONHR$_8$, —NH—CH$_2$—C$_6$H$_4$—R$_9$, —CH$_2$OH, —CH$_2$SO$_2$R$_7$, —CONHR$_8$, halogen or —CN, $R_3$ is H, halogen, R$_7$ or —OR$_7$, $R_2$ and $R_3$, together with each other are

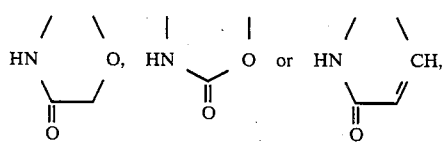

$R_4$ is H, —CH$_3$ or —C$_2$H$_5$, $R_5$ and $R_6$ are each H or —CH$_3$, $R_7$ is C$_1$–C$_4$ alkyl, $R_8$ is H or C$_1$–C$_4$ alkyl, $R_9$ is H, C$_1$–C$_4$ alkyl or C$_1$–C$_4$ alkoxy optionally interrupted by oxygen, $R_{10}$ is H, C$_1$–C$_4$ alkyl, phenyl or pyridyl $R_{11}$ and $R_{12}$ are each H, CH$_3$, Cl or OCH$_3$, or together methylenedioxy, X is

or N, and

Z is —CH$_2$ or —CO;

in the form of racemates, enantiomers, diastereoisomeric antipode pairs, as well as non-toxic, pharmacologically acceptable acid addition salts thereof.

A preferred sub-genus thereunder is constituted by compounds of the formula I wherein $R_1$ is H, $R_2$ is H, —OH, —NHSO$_2$CH$_3$, —NHCOR$_8$, —NH-CONHR$_8$, —NH—CH$_2$—C$_6$H$_4$—R$_9$, —CH$_2$OH, CH$_2$SO$_2$CH$_3$, —CONHR$_8$, Cl or F, $R_3$ is H, Cl, —CH$_3$ or —OCH$_3$, $R_2$ and $R_3$, together with each other are,

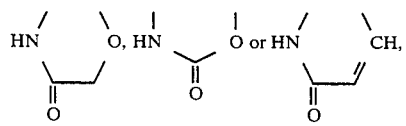

$R_4$ is H, $R_5$, $R_6$, $R_8$ and $R_{10}$, which may be the same or different, are each H or —CH$_3$, $R_9$ is H or 4—OCH$_3$, Het is

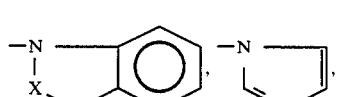

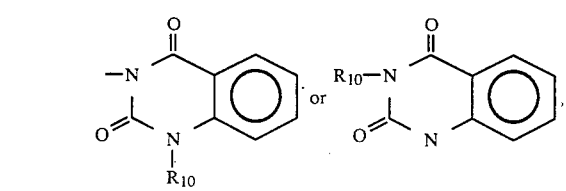

X is —CH= or —N=, and n is an integer from 1 to 4, inclusive, preferably 2 or 3.

The compounds embraced by formula I may be prepared by the following methods:

METHOD A

By reducing an amino-ketone of the formula

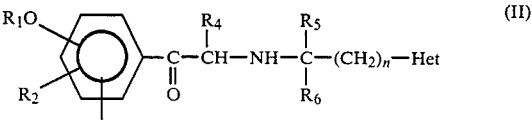

wherein $R_1$ through $R_6$, Het and n have the above-mentioned meanings, and wherein the central nitrogen atom and/or phenolic OH groups present, if any, may be protected by protective groups, separable by hydrogenation, in a suitable solvent with hydrogen and a hydrogenation catalyst or with hydrides having a reducing action, and protective groups still present are optionally removed after the reduction by hydrogenation.

METHOD B

For the preparation of those compounds of the formula I wherein $R_4$ is H, by reacting an amine of the formula

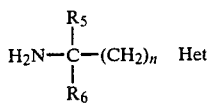  (V)

wherein $R_5$, $R_6$, Het and n have the above-mentioned meanings, under the conditions of reductive amination with a phenyl-glyoxal of the formula

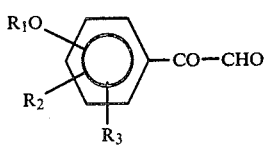  (VI)

wherein $R_1$, $R_2$ and $R_3$ have the above-mentioned meanings, and in which phenolic OH groups present, if any, may be protected by protective groups separable by hydrogenation, optionally in the form of a hemi-acetal, and optionally separating protective groups present by hydrogenation.

METHOD C

By removing the protective group or groups from a compound of the formula

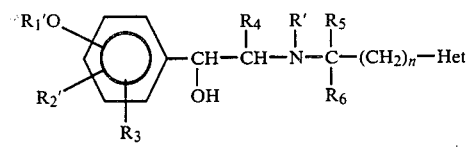  (XI)

wherein $R_3$ to $R_6$, n and Het have the above-mentioned meanings and R' is H or a protective group separable by hydrogenation, $R_1'$ is $R_1$ or a protective group separable by hydrogenation, $R_2'$ is $R_2$, but in the definition thereof of $R_1$ is to be replaced by $R_1'$, and wherein at least one of the radicals $R_1'$ and $R_2'$ is a protective group to be removed.

The end products obtained by methods A, B and C may, if desired, be separated into their enantiomers, optionally also into their diastereoisomeric antipode pairs, if desired, bases obtained may be converted into acid addition salts, and acid addition salts obtained may be converted into the free bases or into salts with other acids.

In method A, solvents which are sufficiently inert under the reaction conditions, for example alcohols such as methanol or ethanol, and conventional hydrogenation catalysts, for example palladium, platinum or Raney nickel are used. Hydrides which may be used as reducing agents are sodium borohydride and other complex hydrides, or diborane. The reaction temperature lies between about 0° C. and the boiling point of the reaction mixture. If the central amino group (contained in the side chain) or the substituents $R_1O$ and/or $R_2$ in the starting starting material have a protecting group separable by hydrogenation, for example an optionally substituted benzyl group, attached thereto, this protective group is removed during, or, if necessary, after the reduction of the —CO— group.

The starting materials of the formula II are obtained, for example, by reaction of amines of the formula III with bromo-ketones of the formula IV in solvents, such as acetonitrile or ethyl acetate, in the presence of an acid-binding agent, such as sodium carbonate, or an excess of the amine:

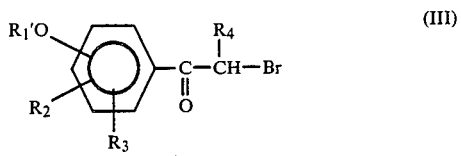  (III)

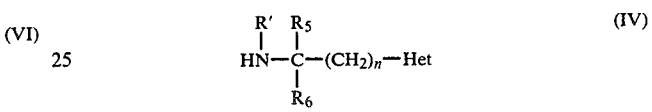  (IV)

wherein $R_1'$ is $R_1$ or a radical separable by hydrogenation, such as benzyl, R' is H or a radical separable by hydrogenation, such as benzyl, and the remaining substituents are as defined above.

In method B it is possible to use compound VI also in the form of a hemi-acetal, that is, in the form of a compound of the formula

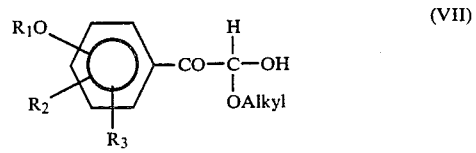  (VII)

wherein $R_1$, $R_2$ and $R_3$ have the above-mentioned meanings and alkyl represents an optionally substituted, preferably $C_1$-$C_6$ alkyl radical.

The Schiff's bases of the formula VIII possibly occurring as intermediate compounds

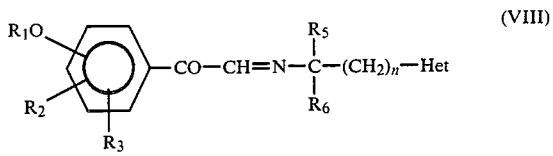  (VIII)

wherein the individual substituents are as defined above, may also be isolated and then subjected to reduction.

Complex hydrides, preferably sodium borohydride or hydrogen in the presence of hydrogenation catalysts, such as platinum, palladium or Raney nickel, are used as reducing agents. If $R_1O$ and/or $R_2$ are phenolic OH groups which are protected by a group separable by hydrogenation, such as benzyl, these groups are, if necessary, removed in the conventional way after reduction.

The amines of the formula are accessible, for example, by alkylating a heterocycle Het-H on the amino group with a compound of the formula

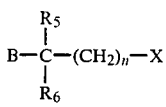

wherein $R_5$ and $R_6$ have the meanings previously defined,

X is chlorine, bromine, methylsulfonic or tolylsulfonic acid radical, and

B is a functional group, such as $NO_2$, dibenzylamino or benzalamino, which may be converted into the amino group by catalytic hydrogenation or hydrolysis in the presence of sodium hydride in solvents such as hexamethyl phosphoric acid triamide, and by converting thereafter the functional radical B into the amino group.

The phenyl glyoxals of the formula VI or the corresponding hemi-acetals of the formula VII may be obtained, for example, by oxidation of an acetophenone of the formula

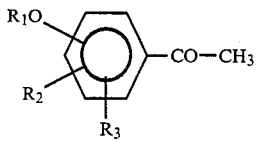

wherein $R_1$, $R_2$ and $R_3$ are as defined above, with selenium dioxide in aqueous dioxane and crystallization from water or alcohols.

In mehod C separation of the protective groups is effected with hydrogen and hydrogenation catalysts, such as palladium, platinum or Raney nickel, at temperatures between 0° C. and the boiling point of the reaction mixture. Lower alkanols, primarily methanol, serve preferably as solvents.

The starting materials of the formula XI may be prepared according to method A or B. Another possibility consists of converting precursors of $R_2'$ in formula XI into $R_2'$ in compounds of the formula

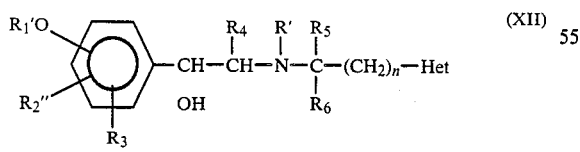

in which n, Het, R', $R_1'$ and $R_3$ to $R_6$ have the above-mentioned meanings and $R''_2$ is a precursor of NH—CONH—$R_8$, NHCOR$_8$, NHSO$_2$R or NH—CH$_2$—C$_6$H$_4$—R$_9$ (e.g. NH$_2$), or of CH$_2$OH or CONHR$_8$ (e.g. COOC$_2$H$_5$), by conventional methods.

Thus, from compounds of the formula XII where $R_2''$ is NH$_2$, compounds of the formula XI wherein $R_2'$ is NHCONH$_2$ may be obtained with potassium cyanate, or the compounds of the formula XI where $R_2'$ is NH—COR$_8$ may be obtained with compounds of the formula $(R_8CO)_2O$. Compounds of the formula XII where $R_2''$ is COOC$_2$H$_5$ yield by reduction with lithium aluminum hydride compounds of the formula XI where $R_2'$ is CH$_2$OH and by reaction with amines of the formula H$_2$NR$_8$ compounds of the formula XI where $R_2'$ is CONHR$_8$ may be obtained.

The following examples illustrate the present invention and will enable others skilled in the art to understand it more completely. It should be understood, however, that the invention is not limited solely to the particular examples given below.

The compounds embraced by formula I are organic bases and therefore form acid addition salts with inorganic or organic acids. Examples of non-toxic, pharmacologically acceptable acid addition salts are those formed with hydrochloric acid, cyclamic acid, maleic acid, sulfuric acid, formic acid, succinic acid, methanesulfonic acid, cyclohexanesulfamic acid, fumaric acid, benzoic acid or the like.

EXAMPLE 1

1-(4-Hydroxy-phenyl)-2-[3-(1-benzimidazolyl)-propylamino]ethanol and its dihydrochloride by method A 30.5 gm of 2-bromo-p-benzyloxyacetophenone and 35 gm of 1-aminopropyl-benzimidazole were stirred for 1 hour at 30°–40° C. in 150 ml of acetonitrile. After separation of the hydrobromide, the mother liquor was acidified with 12 gm of maleic acid, and the precipitated α-[3-(1-benzimidazolyl)propylamino]-4-benzyloxyacetophenone maleate (m.p. 145°–148° C.) was collected by suction of filtiation. Aqueous ammonia was used to prepare the base, which was reduced in 200 ml of alcohol with sodium borohydride to form 1-(4-benzyloxyphenyl)-2-[3-(1-benzimidazolyl)-propylamino]-ethanol (m.p. 83°–85° C.).

Catalytic hydrogenation of 7 gm of this compound in 100 ml of methanol with 1 gm of palladium charcoal as the catalyst yielded 4.5 gm of 1-(4-hydroxyphenyl)-2-[3-(1-benzimidazolyl)-propylamino]-ethanol (m.p.146°–148° C., 83% of theory), whose dihydrochloride of the formula

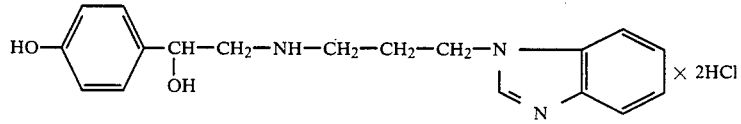

had a melting point of 184°–185° C.

EXAMPLE 2

1-[3-(3-Carbamoyl-4,β-dihydroxy-phenethylamino)-propyl]-1-H-benzotriazole and its cyclamate by method A A mixture of 17.5 gm of 2-benzyloxy-5-bromoacetyl salicylamide, 17.6 gm of 1-(3-aminopropyl)-1H-benzotriazole, 6 gm of sodium carbonate and 150 ml of ethyl acetate was refluxed for 1.5 hours. After separation of the inorganic constituents, the mother liquor was evaporated, the residue was dissolved in a 100 ml of acetonitrile, and the solution was acidified with 5 gm of oxalic acid. The precipitated 1-[3-(3-carbamoyl-4-benzyloxy-β-oxophenethylamino)-propyl]-1-H-benzotriazole oxalate was collected by suction of filtration converted with aqueous ammonia into the base (m.p. 186°–188° C.) and reduced in 100 ml of ethanol with sodium borohydride to form 1-(3-carbamoyl-4-benzyloxy-β-hydroxyphenethylamino)propyl]-1-H-benzotriazole.

Hydrogenation of 6 gm of this compound in 100 ml of methanol at a pressure of 6 bars and 40° C. in the presence of palladium charcoal yielded 3 gm of 1-[3-(3-carbamoyl-4,β-dihydroxy-phenethylamino)-propyl]-1-H-benzotriazole (m.p. 154°–155° C.), 77.5% of theory) whose cyclamate of the formula

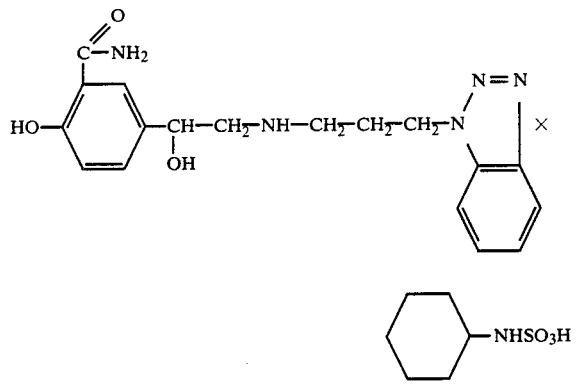

had a melting point of 165° C.

EXAMPLE 3

1-[3-Carbamoyl-4-β-dihydroxy-phenethylamino)-propyl]-3-methylquinazoline-2,4-dione dihydrochloride by method A A mixture of 12.9 gm of 5-bromoacetyl salicylamide, 15.45 gm of 1-(3-benzylaminopropyl)-3-methyl-quinazoline-2,4-dione, 6 gm of sodium carbonate and 300 ml of acetonitrile was refluxed for 1.5 hours. After suction-filtering off the inorganic constituents, the mother liquor was evaporated, the residue was dissolved in 500 ml of methanol, and the solution was hydrogenated, after addition of 12 ml of benzyl chloride, at 6 bars and 60° C. with palladium charcoal as the catalyst. After 2 mols of hydrogen had been taken up, the hydrogenation was complete, and the resulting 1-[3-(3-carbamoyl-β-oxo-4-hydroxyphenethylamino)-phenyl]-3-methyl-quinazoline-2,4-dione hydrochloride (m.p.=253° C. with decomposition) was isolated.

Catalytic hydrogenation of 13 gm of this compound in 250 ml of a methanol/water mixture 1:1 at 6 bars pressure and 50° C. with palladium as the catalyst yielded 8 gm of 1-[3-(3-carbamoyl-4-β-dihydroxy-phenethylamino)-propyl]-3-methylquinazoline-2,4-dion hydrochloride of the formula

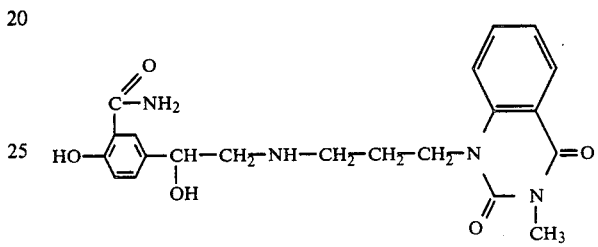

which had a melting point of 220°–221° C. The yield was 61.5% of theory.

Using procedures analogous to those described in Examples 1 to 3, the following compounds of the formula I was also prepared:

TABLE I

| Formula | Yield (%) | Salt with | Melting point in °C. |
|---|---|---|---|
| HO-, HO-⟨⟩-CH(OH)-CH₂-NH-CH₂-CH₂-N=⟨⟩(N) | 88 | 2 × maleic acid | 178–180 |
| HO-, HO-⟨⟩-CH(OH)-CH₂-NH-CH₂-CH₂-CH₂-N=⟨⟩(N) | 61 | Sulphuric acid × 2H₂O | 199–202 |
| HO-, CH₃, HO-⟨⟩-CH(OH)-CH₂-NH-CH₂-CH₂-CH₂-N=⟨⟩(N) | 65 | Sulphuric acid × 0.5 H₂O | 174–176 163 (Base) |
| HO-⟨⟩-CH(OH)-CH₂-NH-C(CH₃)₂-CH₂-CH₂-N-N=N-⟨⟩ | 80 | Formic acid | 158–160 |

TABLE I-continued

| Formula | Yield (%) | Salt with | Melting point in °C. |
|---|---|---|---|
| [structure: 3-NHCOCH₃-4-HO-phenyl-CH(OH)-CH₂-NH-C(CH₃)₂-CH₂-CH₂-N-benzimidazolyl] | 60 | 1.5 × succinic acid | 154–156 |
| [structure: 4-HO-phenyl-CH(OH)-CH₂-NH-C(CH₃)₂-CH₂-CH₂-N-benzimidazolyl] | 83 | 2 × maleic acid | 137–140 |
| [structure: 3-NHSO₂CH₃-4-HO-phenyl-CH(OH)-CH₂-NH-CH₂-CH₂-CH₂-N-(3-methyl-2,4-dioxoquinazolinyl)] | 60 | Methanesulphonic acid | 178–180 |
| [structure: 4-HO-phenyl-CH(OH)-CH₂-NH-C(CH₃)₂-CH₂-CH₂-N-(2,4-dioxoquinazolinyl)] | 80 | Formic acid | 163–166 |
| [structure: 3-NHSO₂CH₃-4-HO-phenyl-CH(OH)-CH₂-NH-C(CH₃)₂-CH₂-CH₂-CH₂-N-benzimidazolyl] | 65 | Cyclohexane sulphaminic acid | 174–176 |

EXAMPLE 4

1-(2,5-Dichloro-4-hydroxy-phenyl)-2-[4-(1-benzimidazolyl)-2-methyl-2-butylamino]-ethanol dihydrochloride by method B A mixture of 9.3 gm of 2,5-dichloro-4-hydroxyphenylglyoxal hydrate, 7.25 gm of 1-(3-amino-3-methylbutyl)-benzimidazole and 100 ml of alcohol was stirred for 3 hours at 40°–45° C. The resulting solution was subsequently cooled, admixed in portions with 8 gm of sodium borohydride, and the mixture was stirred for 3 hours at room temperature. After the addition of 100 ml of methanol for decomposition of the sodium borohydride, the mixture was allowed to stand for 10 hours, the solvent was distilled off under reduced pressure, the residue was dissolved in 200 ml of water, and the solution was acidified with concentrated hydrochloric acid. 9.5 gm of 1-(2,5-dichloro-4-hydroxyphenyl)-2-[4-(1-benzimidazolyl)-2-methyl-2-butylamino]-ethanol dihydrochloride×1H₂O, m.p. 180°–183° C., of the formula

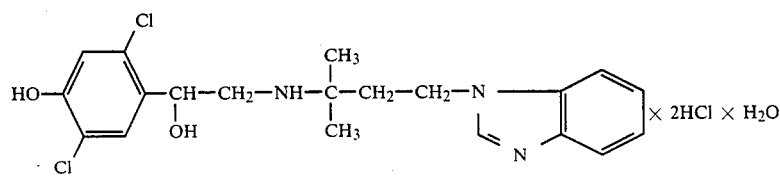

were obtained. The yield was 50.4% of theory.

EXAMPLE 5

2'-Hydroxy-5'-[1-hydroxy-2-[4-(1-benzimidazolyl)-2-methyl-2-butylamino]-ethyl]-methanesulfonanilide and its formate by method B A mixture of 14.4 gm of 2'-benzyloxy-5'-(1-oxo-2-hydroxy-2-ethoxy-ethyl)-methanesulfonanilide, 7 gm of 1-(3-amino-3-methylbutyl)-benzimidazole and 150 ml of alcohol was heated for 3 hours at 50° C. and then admixed in portions with 9.2 gm of sodium borohydride. The resulting solution is kept for 12 hours at room temperature, the alcohol is then removed under reduced pressure on a Rotavapor, and the residue is dissolved with 200 ml of water and 500 ml of ethyl acetate. After decomposition of the sodium borohydride by stirring with concentrated hydrochloric acid and ice cooling, the mixture was made alkaline with aqueous ammonia, and the ethyl acetate phase was separated, dried with sodium sulfate and evaporated on a Rotavapor. The residue was dissolved in 200 ml of alcohol, the solution was acidified with 6.3 gm of oxalic acid, and the precipitated 2'-benzyloxy-5'-[1-hydroxy-2-[4-(1-benzimiazolyl)-2-methyl-2-butylamino]-ethyl]methane sulfonanilide dioxalate (m.p. 185°–187° C.) is extracted. The base (m.p. 65°–70° C.) was liberated from this compound with aqueous ammonia. Catalytic hydrogenation of this compound (m.p. 65°–70° C.) in 250 ml of methanol under standard conditions with palladium charcoal as a catalyst yielded 8 gm of 2'-hydrox-5'-[1-hydroxy-2-[4-(1-benzimidazolyl)-2-methyl-2-butylamino]-ethyl]-methanesulfonanilide (m.p. 170°–173° C.; 81% of theory) whose formates of the formula

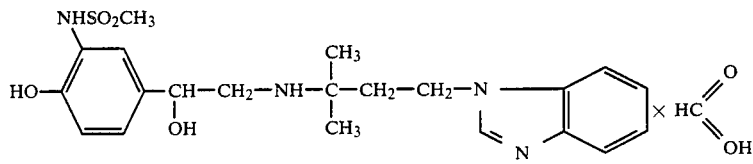

had a melting point of 161°–164° C.

EXAMPLE 6

1-(2-Fluoro-4-hydroxy-phenyl)-2-[4-(1-benzimidazolyl)-2-methyl-2-butylamino]-ethanol and its formate by method B A solution of 15.2 gm of 1-(2-fluoro-4-benzyloxy-phenyl)-1-oxo-2-hydroxy-2-ethoxy-ethane in 200 ml of alcohol was admixed with 8.2 gm of 1-(3-amino-3-methylbutyl)-benzimidazole, and the mixture was stirred for 3 hours at 50° C. The resulting solution was subsequently cooled, admixed with 4 gm of sodium borohydride and stirred for 6 hours at room temperature. The mixture was then worked up as described in Example 3. The residue was dissolved in 200 ml of alcohol, the solution was acidified with 7.2 gm of oxalic acid, and the precipitated 1-(2-fluoro-4-benzyloxy-phenyl)-2-[4-(1-benzimidazolyl)-2-methyl-2-butylamino]-ethanol dioxalate (m.p. 184°–188° C.) was suction filtered off. The base (m.p. 85°–88° C.) was liberated from the dioxalate with aqueous ammonia.

Catalytic hydrogenation of this compound in 250 ml of methanol at 6 bars pressure with palladium charcoal as the catalyst at about 30° C. yielded 1-(2-fluoro-4-hydroxyphenyl)2-[4-(1-benzimidazolyl)-2-methyl-2-butylamino]-ethanol, m.p. 151°–153° C., whose formate of the formula

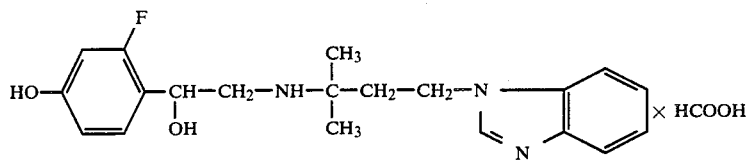

had a melting point of 157°–159° C.

By addition of the calculated quantity of methanesulfonic acid to the solution of the base in ethanol and the methanesulfonate, m.p. 178°–179° C. was obtained. The hydrochloride was prepared correspondingly, m.p. 205° C. The dihydrochloride tetrahydrate, m.p. 177° C., was obtained from the base in aqueous acetonitrile was the calculated quantity of concentrated hydrochloric acid. The sulfhate hydrate, m.p. 207°–208° C. was obtained analogously in aqueous ethanol.

Using procedures analogous to those described in Examples 4 to 6, the following compounds of the formula I were also prepared.

TABLE II

| Formula | Yield (%) | Salt with | Melting point °C. |
|---|---|---|---|
| ![structure] | 79.5 | Formic acid | 128 |
| ![structure] | 85 | Methanesulphonic acid | 178–180 / 123 Base |

TABLE II-continued

| Formula | Yield (%) | Salt with | Melting point °C. |
|---|---|---|---|
| HO-C6H2(CH3)(OH)-CH(OH)-CH2-NH-CH2-CH2-N(CH2CH2)C(=O)NH (imidazolidinone) | 54.5 | Cyclohexane-sulphaminic acid | 177–179<br>171 Base |
| HO-C6H2(CH3)(OH)-CH(OH)-CH2-NH-C(CH3)2-CH2-CH2-N (quinazoline-2,4-dione) | 79 | 2 × formic acid ×<br>1 H₂O | 174–176<br>188–190 Base |
| HO-C6H4-CH(OH)-CH2-NH-C(CH3)2-CH2-CH2-N (quinazoline-2,4-dione) | 83 | Formic acid | 163–166<br>193–196 Base |
| HO-C6H4-CH(OH)-CH2-NH-C(CH3)2-CH2-CH2-N(CH2CH2)C(=O)NH | 93 | 0.5 succinic acid | 187–189<br>168–172 Base |
| HO-C6H4-CH(OH)-CH2-NH-C(CH3)2-CH2-CH2-N (benzimidazole) | 85 | Sulphuric acid ×<br>1 H₂O | 173–175<br>174–176 Base |
| CH2SO2CH3, HO-C6H3-CH(OH)-CH2-NH-C(CH3)2-CH2-CH2-N (benzimidazole) | 93 | Maleic acid | 190–193<br>181–183 Base |
| CH2SO2CH3, HO-C6H3-CH(OH)-CH2-NH-CH2-CH2-CH2-N (benzotriazole) | 50 | Cyclohexane-sulphaminic acid | 162–164 |
| HO-C6H2(CH3)(OH)-CH(OH)-CH2-NH-C(CH3)2-CH2-CH2-CH2-N (benzimidazole) | 58 | Sulphuric acid | 224–226 decomp. |
| NC-C6H3(OH)-CH(OH)-CH2-NH-C(CH3)2-CH2-CH2-N (methylbenzimidazole) | 48.5 | hydrochloric acid | 208–210 decomp. |

TABLE II-continued

| Formula | Yield (%) | Salt with | Melting point °C. |
|---|---|---|---|
| (3-CN, 4-OH-C₆H₃)-CH(OH)-CH₂-NH-CH₂-CH₂-CH₂-N(benzotriazolyl) | 69 | hydrochloric acid | 208–210 |
| (4-OH-C₆H₄)-CH(OH)-CH₂-NH-C(CH₃)₂-CH₂-CH₂-N(benzotriazolyl) | 86 | Formic acid | 158–160<br>129–132 Base |
| (3-NHSO₂CH₃, 4-OH-C₆H₃)-CH(OH)-CH₂-NH-C(CH₃)₂-CH₂-CH₂-N(benzotriazolyl) | 92 | Hydrochloric acid | 203–204 decomp.<br>165–167 Base |
| (3-OH, 2-CH₃, 4-OH-C₆H₂)-CH(OH)-CH₂-NH-C(CH₃)₂-CH₂-CH₂-N(benzotriazolyl) | 77.5 | Cyclohexane-sulphaminic acid | 177–180 |
| (3-NHCOCH₃, 4-OH-C₆H₃)-CH(OH)-CH₂-NH-C(CH₃)₂-CH₂-CH₂-N(benzimidazolyl) | 50 | 1.5 × succinic acid | 154–156 |
| (3-Cl, 4-OH-C₆H₃)-CH(OH)-CH₂-NH-C(CH₃)₂-CH₂-CH₂-N(benzimidazolyl) | 60 | Formic acid × 1 H₂O | 115–119 |
| (4-OH-C₆H₄)-CH(OH)-CH₂-NH-C(CH₃)₂-CH₂-CH₂-N(imidazolyl) | 87.5 | 2 × maleic acid | 137–140<br>165–168 Base |
| (3-CN, 4-OH-C₆H₃)-CH(OH)-CH₂-NH-C(CH₃)₂-CH₂-CH₂-N(imidazolyl) | 62 | 2 × maleic acid | 176–179<br>245 decomp. base |

TABLE II-continued

| Formula | Yield (%) | Salt with | Melting point °C. |
|---|---|---|---|
| (3,5-dihydroxyphenyl)-CH(OH)-CH₂-NH-C(CH₃)₂-CH₂-CH₂-N(imidazole) | 82 | Sulphuric acid | 287 decomp. 218–220 Base |
| (2-Cl-4-HO-phenyl)-CH(OH)-CH₂-NH-C(CH₃)₂-CH₂-CH₂-N(benzimidazole) | 80 | Maleic acid | 185–186 175–178 Base |
| (3-OCH₃-4-HO-phenyl)-CH(OH)-CH₂-NH-C(CH₃)₂-CH₂-CH₂-N(benzimidazole) | 63 | Maleic acid | 173–174 |
| (2-Cl-4-HO-phenyl)-CH(OH)-CH₂-NH-C(CH₃)₂-CH₂-CH₂-CH₂-N(benzimidazole) | 75 | Maleic acid × ½ Aceton-nitrile | 161–165 160–162 Base |
| (3-NHSO₂CH₃-4-HO-phenyl)-CH(OH)-CH₂-NH-C(CH₃)₂-CH₂-CH₂-CH₂-N(benzimidazole) | 72 | Cyclohexane-sulphaminic acid | 174–176 182–184 Base |
| (2-F-4-HO-phenyl)-CH(OH)-CH₂-NH-C(CH₃)₂-CH₂-CH₂-CH₂-N(benzimidazole) | 81 | Maleic acid | 186–189 155–159 |
| (3-NHCOCH₃-2-OCH₃-6-HO-phenyl)-CH(OH)-CH₂-NH-C(CH₃)₂-CH₂-CH₂-N(benzimidazole) | 77.5 | Fumaric acid | 158–160 |
| (benzoxazinone-substituted phenyl)-CH(OH)-CH₂-NH-C(CH₃)₂-CH₂-CH₂-N(benzimidazole) | 78 | Formic acid × 1 water | 175–178 |

TABLE II-continued

| Formula | Yield (%) | Salt with | Melting point °C. |
|---|---|---|---|
| [structure: 2-carbamate-4-hydroxyphenyl-CH(OH)-CH₂-NH-C(CH₃)₂-CH₂-CH₂-N-benzimidazole] | 73.5 | Maleic acid × ½ ethanol | 167–169 |
| [structure: 2-F-4-HO-phenyl-CH(OH)-CH₂-NH-C(CH₃)₂-CH₂-CH₂-N-(2-CH₃-benzimidazole)] | 77.5 | 2 × hydrochloric acid | 168–170 186–188 Base |
| [structure: 3-NHSO₂CH₃-4-HO-phenyl-CH(OH)-CH₂-NH-C(CH₃)₂-CH₂-CH₂-N-(2-CH₃-benzimidazole)] | 82 | Sulphuric acid | 215–218 decomp. 185–186 Base |
| [structure: 2-F-4-HO-phenyl-CH(OH)-CH₂-NH-C(CH₃)₂-CH₂-CH₂-N-(5,6-diCH₃-benzimidazole)] | 77 | 2 × hydrochloric acid | 185–186 |
| [structure: 3-NHSO₂CH₃-4-HO-phenyl-CH(OH)-CH₂-NH-C(CH₃)₂-CH₂-CH₂-N-(5,6-diCH₃-benzimidazole)] | 93 | 2 × hydrochloric acid | 189–191 182–184 Base |
| [structure: 3-CN-4-HO-6-OCH₃-phenyl-CH(OH)-CH₂-NH-C(CH₃)₂-CH₂-CH₂-N-benzimidazole] | 92.5 | Formic acid | 180–182 125° decomp. Base |
| [structure: 2-F-4-HO-phenyl-CH(OH)-CH₂-NH-C(CH₃)₂-CH₂-CH₂-N-(2-phenyl-benzimidazole)] | 32 | | 148–151 Base |
| [structure: 3-NHSO₂CH₃-4-HO-phenyl-CH(OH)-CH₂-NH-C(CH₃)₂-CH₂-CH₂-N-(4,5-diphenyl-imidazole)] | 74 | Formic acid | 170–172 |

TABLE II-continued

| Formula | Yield (%) | Salt with | Melting point °C. |
|---|---|---|---|
| (structure: 2-fluoro-4-hydroxyphenyl-CH(OH)-CH₂-NH-C(CH₃)₂-CH₂-CH₂-N-imidazole with two phenyl substituents) | 93 | 2 × hydrochloric acid | 165–168 163–165 Base |
| (structure: 3-NHSO₂CH₃, 4-hydroxyphenyl-CH(OH)-CH₂-NH-C(CH₃)₂-CH₂-CH₂-CH₂-N-imidazole with phenyl) | 78.5 | Formic acid | 156–159 133–136 Base |
| (structure: 2-fluoro-4-hydroxyphenyl-CH(OH)-CH₂-NH-C(CH₃)₂-CH₂-CH₂-N-imidazole with phenyl) | 87 | 2 × hydrochloric acid | 210–212 |
| (structure: 3-fluoro-4-hydroxyphenyl-CH(OH)-CH₂-NH-C(CH₃)₂-CH₂-CH₂-N-imidazole with phenyl) | 85 | Formic acid | 160–163 123–125 Base |

EXAMPLE 7

1-{3-[2-Hydroxy-2-(4-hydroxy-phenyl)-ethylamino]-propyl}-1,2,3,4-tetrahydro-4-quinazolone and its formate by method C 15.5 gm of 1-{-[2-hydroxy-2-(4-benzyloxy-phenyl)-benzylethylamino]-propyl}-1,2,3,4-tetrahydro-4-quinazolone (m.p. 119°–121° C.) were dissolved in 250 ml of methanol and debenzylated by hydrogenation at 60° C. and 6 bars pressure in the presence of palladium as the catalyst. After 2 mols of hydrogen had been taken up, the hydrogenation was complete, yielding of 8 gm of 1-{3-[2-hydroxy-2-(4-hydroxyphenyl)ethylamino]-propyl}-1,2,3,4-tetrahydro-4-quinazolone, whose formate of the formula

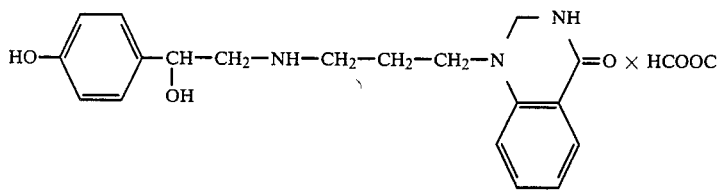

had a melting point of 174°–176° C. The yield was 61.5% of theory.

EXAMPLE 8

1-{2'-Hydroxy-5'-[1-hydroxy-2-[4-(1-imidazolyl)-2-methyl-2-butylamino]-ethyl]-phenyl}-urea and its sulfate by method C A mixture of 15 gm of 2'-benzyloxy-5'-[1-hydroxy-2-[4-(1-imidazolyl)-2-methyl-2-butylamino]-ethyl]-acetanilide (m.p. of the dioxalate 160°–163° C.), 18.5 gm of KOH, 80 ml of alcohol and 15 ml of water was refluxed for 24 hours, and the resulting 1-(3-amino-4-benzyloxy-phenyl)-2-[4-(1-imidazolyl)-2-methyl-2-butylamino]-ethanol was isolated as the trioxalate (m.p. 95°–100° C.). Aqueous ammonia was used to liberate the base which was reacted with potassium cyanate to form 1-{2'-benzyloxy-5'-[1-hydroxy-2-[4-(1-imidazolyl)-2-methyl-2-butylamino]-ethyl]-phenyl}-urea (m.p. 142°–143° C.). Catalytic hydrogenation of 5.1 gm of this compound in 100 ml of methanol with palladium charcoal as the catalyst yielded 3.5 gm of 1-{2'-hydroxy-5'-[1-hydroxy-2-]-4-(1-imidazolyl)-2-methyl-2- butylamino]-ethyl]-phenyl]-phenyl}-urea, whose sulfate of the formula

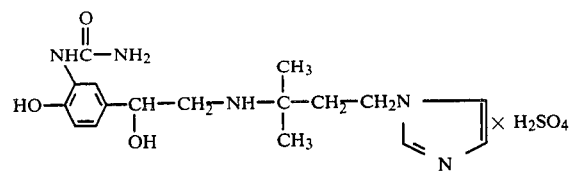

had a melting point of 243°–244° C. The yield was 70% of theory.

EXAMPLE 9

5-[1-Hydroxy-2-[4-(1-imidazolyl)-2-methyl-2-butylamino]-ethyl]-N-methyl-salicylamide sulfate by method C 8.5 gm of methyl 2′-benzyloxy-5′-[1-hydroxy-2-[4-(1-imidazolyl)-2-methyl-4-butylamino]-ethyl]-benzoate (m.p. of the dioxalate 156°–158° C. were hydrogenated under standard conditions in 100 ml of methanol in the presence of palladium as the catalyst, and after 1 mol of hydrogen had been taken up the catalyst was filtered off, and 15 ml of monomethylamine were added to the filtate. After 2 days of standing the solvent was distilled off, the residue was dissolved in 15 ml of alcohol and 15 ml of water, and the solution was acidified with 2 gm of concentrated sulfuric acid.

4.5 gm of 5-[1-hydroxy-2[4-(1-imidazolyl)-2-methyl-2-butylamino]-ethyl]-N-methyl-salicylamide sulfate of the formula

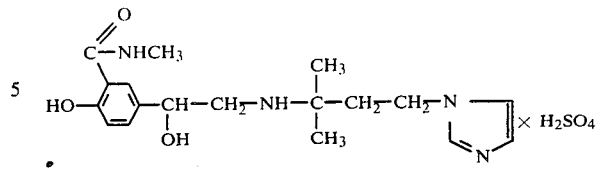

having a melting point of 263°–265° C. (decomposition) were obtained. The yield was 52% of theory.

EXAMPLE 10

1-(3-Hydroxymethyl-4-hydroxy-phenyl)-2-[4-(1-imidazolyl)-2-methyl-2-butylamino]-ethanol and its benzoate by method C 13.5 gm of methyl 2′-benzyloxy-5′-[1-hydroxy-2-[4-(1-imidazolyl)-2-methyl-4-butylamino]-ethyl]-benzoate (m.p. of the dioxalate 156°–158° C.) were reduced in 200 ml of tetrahydrofuran with 6 gm of lithium aluminum hydride to form 1-(3-hydroxymethyl-4-benzyloxy-phenyl)-2-[4-(1-imidazolyl)-2-methyl-2-butylamino]-ethanol, whose dioxalate melted at 144°–146° C. Aqueous ammonia was used to liberate the base from 10 gm of dioxalate, which was hydrogenated in 100 ml of methanol with palladium as the catalyst. 4.5 gm of 1-(3-hydroxymethyl-4-hydroxyphenyl)-2-[4-(1-imidazolyl)-2-methyl-2-butylamino]-ethanol (m.p. 135°–137° C.) were obtained; the benzoate thereof of the formula

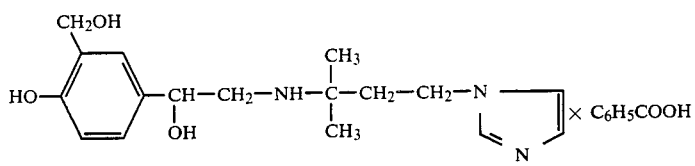

had a melting point of 150°–152° C. The yield was 83% of theory.

Using procedures analogous to those described in Example 7 to 10, the following compounds of the formula I were also prepared:

TABLE III

| Formula | Yield % | Salt with | Melting point °C. |
|---|---|---|---|
| (structure) | 62.5 | Sulphuric acid × 1 water | 183° C. decomp. |
| (structure) | 40 | 2 × fumaric acid | 158–162 |

TABLE III-continued

The following are prepared analogously

| Formula | Yield % | Salt with | Melting point °C |
|---|---|---|---|
| 3-(CONHCH₃)-4-HO-C₆H₃-CH(OH)-CH₂-NH-C(CH₃)₂-CH₂-CH₂-N(benzimidazolyl) | 60.8 | Sulphuric acid | 221–223 |
| 3-(CH₂OH)-4-HO-C₆H₃-CH(OH)-CH₂-NH-C(CH₃)₂-CH₂-CH₂-N(benzimidazolyl) | 52 | Cyclohexane-sulphuric acid | 126–130 |
| 2-OH-3-CH₃-4-HO-C₆H₂-CH(OH)-CH₂-NH-C(CH₃)₂-CH₂-CH₂-N(benzimidazolyl) | 48 | Sulphuric acid | 192–194 decomp. |
| 3,5-(HO)₂-C₆H₃-CH(OH)-CH₂-NH-C(CH₃)₂-CH₂-CH₂-N(benzimidazolyl) | 80 | 2 × hydrochloric acid | 157–159 / 175 Base |
| 4-HO-C₆H₄-CH(OH)-CH₂-NH-CH₂-CH₂-CH₂-N(benzotriazolyl) | 87.5 | formic acid | 167–169 / 144–146 Base |
| 2-OH-3-CH₃-4-HO-C₆H₂-CH(OH)-CH₂-NH-CH₂-CH₂-CH₂-N(imidazolyl) | 71 | 2 × formic acid | 137–138 |
| 2-OH-3-CH₃-4-HO-C₆H₂-CH(OH)-CH₂-NH-CH₂-CH₂-CH₂-N(benzotriazolyl) | 87.5 | Benzoic acid | 165–166 |
| 4-HO-C₆H₄-CH(OH)-CH₂-NH-C(CH₃)₂-CH₂-CH₂-N(benzimidazolyl) | 84 | Formic acid | 182–184 |

TABLE III-continued

*The following are prepared analogously*

| Formula | Yield % | Salt with | Melting point °C. |
|---|---|---|---|
| [structure: 2-NHSO₂CH₃, 4-HO-phenyl-CH(OH)-CH₂-NH-C(CH₃)₂-CH₂-CH₂-N(quinazoline-2,4-dione)] | 79 | Hydrochloric acid | 223–225<br>183–186 Base |
| [structure: 2-OCH₃, 4-HO-phenyl-CH(OH)-CH₂-NH-C(CH₃)₂-CH₂-CH₂-N(quinazoline-2,4-dione)] | 76 | Methanesulphonic acid | 193–194 |
| [structure: 2-F, 4-HO-phenyl-CH(OH)-CH₂-NH-C(CH₃)₂-CH₂-CH₂-N(quinazoline-2,4-dione)] | 95 | Methanesulphonic acid | 186–188<br>127 Base |
| [structure: 2-CH₃, 3-OH, 4-HO-phenyl-CH(OH)-CH₂-NH-CH₂-CH₂-CH₂-N(N-methyl benzamide ring)] | 83 | Hydrochloric acid | 216–271 |
| [structure: 2-NHC(O)NH₂, 4-HO-phenyl-CH(OH)-CH₂-NH-C(CH₃)₂-CH₂-CH₂-N(benzimidazole)] | 45 | Maleic acid | 186–188 |
| [structure: 2-CH₂OH, 4-HO-phenyl-CH(OH)-CH₂-NH-C(CH₃)(CH₂)-CH₂-CH₂-N(benzimidazole)] | 52 | Cyclohexane sulphaminic acid × 1 water | 126–130 |
| [structure: 2-CH₂OH, 4-HO-phenyl-CH(OH)-CH₂-NH-C(CH₃)₂-CH₂-CH₂-N(imidazole)] | 83 | Benzoic acid | 150–152<br>137–137 Base |
| [structure: 2-NHC(O)CH₃, 4-HO-phenyl-CH(OH)-CH₂-NH-C(CH₃)₂-CH₂-CH₂-N(imidazole)] | 70 | Sulphuric acid | 235–236<br>142–145 Base |

TABLE III-continued

*The following are prepared analogously*

| Formula | Yield % | Salt with | Melting point °C. |
|---|---|---|---|
| 5-[CH(OH)-CH$_2$-NH-C(CH$_3$)$_2$-CH$_2$-CH$_2$-N(imidazole)]-2-hydroxy-phenyl urea | 70 | Sulphuric acid | 243-244 |
| N-acetyl-5-[CH(OH)-CH$_2$-NH-C(CH$_3$)$_2$-CH$_2$-CH$_2$-CH$_2$-N(benzimidazole)]-2-hydroxy-aniline | 41 | Benzoic acid × 1 water | 130-133 |
| 5-[CH(OH)-CH$_2$-NH-C(CH$_3$)$_2$-CH$_2$-CH$_2$-CH$_2$-N(benzimidazole)]-2-hydroxy-phenyl urea | 85 | 0,5 × fumaric acid | 192 |
| 3-methoxy-4-hydroxy-[CH(OH)-CH$_2$-NH-C(CH$_3$)$_2$-CH$_2$-CH$_2$-CH$_2$-N(benzimidazole)]-benzene | 63 | Maleic acid | 155-157 |
| 3-methoxy-4-hydroxy-[CH(OH)-CH$_2$-NH-C(CH$_3$)$_2$-CH$_2$-CH$_2$-N(benzimidazole)]-benzene | 73.5 | Sulphuric acid | 187-188 decomp. |
| 8-hydroxy-7-[CH(OH)-CH$_2$-NH-C(CH$_3$)$_2$-CH$_2$-CH$_2$-N(benzimidazole)]-2H-1,4-benzoxazin-3(4H)-one | 76 | 2 × hydrochloric acid × 2 water | 166-168 |
| 2-methoxy-3-(methanesulfonylamino)-4-hydroxy-[CH(OH)-CH$_2$-NH-C(CH$_3$)$_2$-CH$_2$-CH$_2$-N(benzimidazole)]-benzene | 72 | Formic acid | 172-174 |

TABLE III-continued

The following are prepared analogously

| Formula | Yield % | Salt with | Melting point °C. |
|---|---|---|---|
| HN-C(=O)-O- attached to HO-phenyl-CH(OH)-CH₂-NH-C(CH₃)₂-CH₂-CH₂-N-indole | 60 | 2 × hydrochloric acid | 200° C. decomp. |

The compounds of the present invention, that is, those embraced by formula I above and their non-toxic, pharmaceutically acceptable acid addition salts, have useful pharmaceodynamic porperties. More particularly, they exhibit broncholytic, spasmolytic and antiallergic activity, and may therefore be used for the treatment of bronchitis, asthma, urticaria, conjunctivitis, hay fever and cold ailments, also as relaxants of the muscles of the uterus, for example in prenatal complaints. Furthermore, the novel compounds are suitable for treatment of cardiovascular disturbances such as high blood pressure, diseases of the peripheral vessels and cardiac arrhythmia.

Mention must be made, finally, of their inhibiting activity on gastro-secretion and the primary anti-depressive activity on the central nervous system.

To be emphasised is the strong and long-lasting broncholytic activity which is associated with only small secondary effects on the heart and skeleton musculature.

The compounds of the formula I where $R_2$ is $CONHR_8$ exhibit hypotensive activity, while the remaining compounds exhibit the other activities specified.

The therapeutic dose is dependent on the compound used, on the nature of the condition, on the type of administration and also on the body weight, if local application is not adopted.

The following are effective daily doses for an adult: For broncholysis: orally 2–20 mg, by inhalation 0.1–1.5 mg, subcutaneously 0.2–1.5 mg. For uterine spasmolysis: orally 10–50 mg, as an infusion solution 0.1–1 mg in ampoules with 10 ml solution. For vasodilation: orally 20–100 mg, in the form of solutions for intramuscular injection 20–40 mg. As a hypotensive agent: orally 200–1800 mg.

For administration the conventional galenic preparations, for example capsules, tablets, coated tables, solutions, suspensions, powders, creams, ointments, emulsions and sprays, are prepared from the compounds according to the invention. In pulmonary administration, powders with a particle diameter of 0.5 to 7 μm are preferably introduced into the bronchial region as an aerosol with breathing air, optionally also with additioal propellent gases.

Parenteral application is effected preferably in the form of sterile isotonic aqueous solutions, while primarily lotions, creams, ointments, emulsions and sprays serve for local application.

The favorable levels of activity of the compounds according to the invention are demonstrated by the following data.

1. Bronchospasmolysis

The activity was tested on guinea pigs under urethane anaesthesia. Body plethysmography was used to determine the influence on acetylcholine bronchospasm after intravenous and oral application. Furthermore, the heart frequency was monitored.

| Compound | Broncholysis $ED_{50}$ ug/kg intravenous | oral | Resorption ratio oral/intravenous |
|---|---|---|---|
| Table III, 16th compound | 1.2 | 7.6 | 6.3 |
| Table II, 16th compound | 1.8 | 66 | 37 |
| Table III, 15th compound | 0.9 | 14 | 16 |
| Table II, 21st compound | 7.6 | 190 | 25 |
| Example 6 | 3.6 | 7 | 1.9 |
| Table III, 24th compound | 0.09 | 5.4 | 60 |
| Salbutamol | 9.2 | 1000 | 109 |

The compounds according to the invention show an outstanding relationship between intravenous and oral activity. The influence on heart rat is simultaneously small. Furthermore, the toxicity is so low that a considerable therapeutic spectrum is obtained; for example, for the compound according to Example 6 the $LD_{50}$ in mice is 29 mg/kg i.v and 300 mg/kg p.o.

2. Uterine relaxation

Uterine relaxation was investigated on anesthetized rats. The intravenous $ED_{50}$ of uterine relaxation was determined in ug/kg (50% of the tested animals react) and the (undesirable) increase in heart rate at the $ED_{50}$ value was also determined. The comparison compound was fenoterol.

| Compound | Uterine relaxation $ED_{50}$ (g/kg) i.v. | Increase in heart rate (beats per min.) | Increase in heart rate in comparison with fenoterol |
|---|---|---|---|
| Table III 10th compound | 0.82 | 19 | ½ |
| Table II, 11th compound | 0.76 | 18 | ½ |
| Table II, 15th compound | 0.44 | 23 | ⅔ |
| Table II, 24th compound | 0.5 | 18 | ½ |
| Fenoterol | 0.45 | 36 | 1 |

The compounds according to the invention thus bring about upon application of the $ED_{50}$ of uterine relaxation a considerably smaller increase of heart rate than the commercial product fenoterol.

The following illustrate a few pharmaceutical dosage unit compositions comprising a compound of the present invention as an active ingredient and represent the best modes contemplated of putting the invention into practical use.

| Tablets | |
|---|---|
| Composition of one tablet: | |
| Active substance according to the invention | 20 mg |
| Colloidal silicic acid | 10 mg |
| Lactose | 118 mg |
| Potato starch | 60 mg |
| Polyvinyl pyrrolidone | 6 mg |
| Sodium cellulose glycolate | 4 mg |
| Magnesium stearate | 2 mg |
| | 220 mg |
| Ampules | |
| Composition of the solution per ampule: | |
| Active substance according to the invention | 10 mg |
| Sorbitol | 40 mg |
| Distilled water q.s. ad | 10 ml |
| Suppositories | |
| Composition per suppository: | |
| Active substance according to the invention | 100 mg |
| Suppository base (cocoa butter) | 1600 mg |
| | 1700 mg |

Inhalation powder 0.5 mg of active substance according to the invention and 19.5 mg of lactose with a particle diameter between 0.5 and 7 μm are used for each hard gelatine capsule.

The active substances according to the invention may also be combined with known active substances; for broncholytic application, for example with theophyllines, prasympatholytics (e.g. ipratropium bromide), secretolytics (e.g. bromohexine), musculotropic spasmolytics (e.g. papaverine), corticosteroids, anti-allergic agents. With uterine relaxants among others combinations with corticosteroids are possible. While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

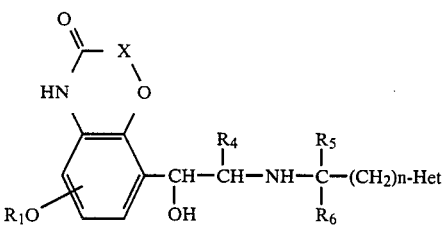

wherein
Het is

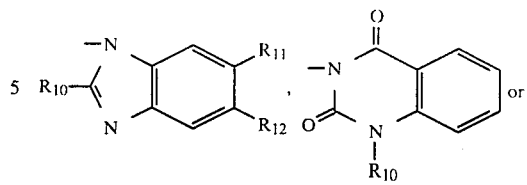

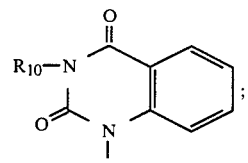

n is 1, 2, 3 or 4;
X is a direct single bond or —CH$_2$—;
R$_1$ is hydrogen or acyl;
R$_4$ is hydrogen, methyl or ethyl;
R$_5$ and R$_6$ are each independently hydrogen or methyl;
R$_{10}$ is hydrogen, alkyl of 1 to 4 carbon atoms, phenyl or pyridyl; and
R$_{11}$ and R$_{12}$ are each independently hydrogen, methyl, chlorine or methoxy; or
R$_{11}$ and R$_{12}$, together with each other, are methylenedioxy;
or a non-toxic, pharmacologically acceptable acid addition salt thereof.

2. A compound of claim 1, where
Het is

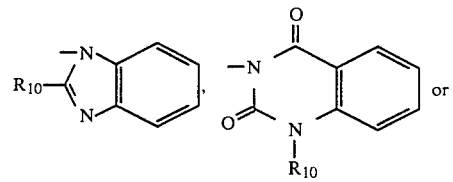

n is 1, 2, 3 or 4;
X is a direct single bond or —CH$_2$—;
R$_1$ and R$_4$ are hydrogen; and
R$_5$, R$_6$ and R$_{10}$ are each independently hydrogen or methyl; or a non-toxic, pharmacologically acceptable acid addition salt thereof.

3. A compound of claim 1, where n is 2 or 3.

4. A compound of claim 2, where n is 2 or 3.

5. An antispasmodic or antiallergic pharmaceutical dosage unit composition consisting essentially of an inert pharmaceutical carrier and an effective antispasmodic or antiallergic amount of a compound of claim 1.

6. The method of relieving spasmodic activity in a warm-blooded animal in need thereof, which comprises perorally, parenterally or rectally administering to said animal an effective antispasmodic amount of a compound of claim 1.

* * * * *